United States Patent
Hornung et al.

(10) Patent No.: US 6,759,103 B2
(45) Date of Patent: Jul. 6, 2004

(54) FLUORINATED CYCLOPENTA[B] NAPHTHALENES AND THEIR USE IN LIQUID-CRYSTAL MIXTURES

(75) Inventors: Barbara Hornung, Hasselroth (DE); Wolfgang Schmidt, Drcieich (DE); Rainer Wingen, Hattersheim (DE)

(73) Assignee: Clariant Financi (BVI) Limited (VG)

( * ) Notice: Subject to any disclaimer, the term of this patent is extended or adjusted under 35 U.S.C. 154(b) by 84 days.

(21) Appl. No.: 10/241,881

(22) Filed: Sep. 12, 2002

(65) Prior Publication Data

US 2003/0091756 A1 May 15, 2003

(30) Foreign Application Priority Data

Sep. 17, 2001 (DE) .......................................... 101 45 779

(51) Int. Cl.[7] .......................... C09K 19/32; C09K 19/30; C09K 19/34; C07C 25/18; C07D 319/06
(52) U.S. Cl. .............. 428/1.1; 252/299.61; 252/299.62; 252/299.63; 252/299.67; 570/183; 570/187; 549/369
(58) Field of Search ........................ 252/299.61, 299.62, 252/299.63, 299.67; 549/369; 570/183, 187; 428/1.1

(56) References Cited

U.S. PATENT DOCUMENTS

| | | | |
|---|---|---|---|
| 4,798,680 A | 1/1989 | Nohira et al. | 252/299.01 |
| 5,384,065 A | 1/1995 | Geelhaar et al. | 252/299.63 |
| 5,550,236 A | 8/1996 | Schlosser et al. | 544/238 |
| 5,744,060 A | 4/1998 | Tarumi et al. | 252/299.63 |
| 5,800,734 A | 9/1998 | Buchecker et al. | 252/299.61 |
| 5,997,766 A | 12/1999 | Kirsch et al. | 252/299.61 |
| 6,083,573 A | 7/2000 | Tarumi et al. | 428/1.1 |
| 6,159,561 A | 12/2000 | Schmidt et al. | 428/1.1 |
| 6,406,761 B1 | 6/2002 | Tarumi et al. | 428/1.1 |
| 2001/0050352 A1 | 12/2001 | Wingen et al. | 252/299.5 |

FOREIGN PATENT DOCUMENTS

| | | |
|---|---|---|
| DE | 44 27 266 | 2/1995 |
| DE | 195 28 085 | 2/1996 |
| DE | 195 28 665 | 2/1997 |
| DE | 196 29 812 | 2/1997 |
| DE | 195 32 292 | 3/1997 |
| DE | 196 07 996 | 9/1997 |
| DE | 196 54 487 | 7/1998 |
| DE | 198 40 447 | 3/2000 |
| DE | 198 57 352 | 6/2000 |
| DE | 100 50 071 | 6/2001 |
| DE | 100 26 661 | 11/2001 |
| EP | 0 318 423 | 5/1989 |
| EP | 0 343 830 | 11/1989 |
| EP | 0 474 062 | 3/1992 |
| EP | 0 665 825 | 8/1995 |
| EP | 0 736 513 | 10/1996 |
| EP | 0 952 135 | 10/1999 |
| WO | WO 92/11241 | 7/1992 |
| WO | WO 94/26692 | 11/1994 |
| WO | WO 96/00710 | 1/1996 |
| WO | WO 96/30344 | 10/1996 |

OTHER PUBLICATIONS

CAPLUS 2003: 257327.*
English abstract for EP 0318423, May 31, 1989.
English abstract for WO 92/11241, Jul. 9, 1992.
English abstract for DE 4427266, Feb. 9, 1995.
English abstract for DE 19528085, Feb. 8, 1996.
English Abstract for DE 19607996, Sep. 11,1997.
English abstract for DE 19840447, Mar. 9, 2000.
English abstract for DE 19857352, Jun. 15, 2000.
English abstract for DE 10050071, Jun. 28, 2001.
Ichinose, H., et al., "High optical anisotrophy and small rotational viscosity LC mixture for field–sequential color TN–LCDs", Seventh International Display Workshop, Nov. 25–Dec. 1, 2000, Kobe, Japan, IDW '00, pp. 77–80.
Meyer, A.Y., et al., "Planar and nonplanar unsaturation, preparation, properties, and molecular–orbital characterization of some fluoro–derivative of anthracene and anthraquinone", Israel Journal of Chemistry, vol. 11, No. 6, 1973, pp. 791–804.

(List continued on next page.)

Primary Examiner—Shean C. Wu
(74) Attorney, Agent, or Firm—Alan P. Kass

(57) ABSTRACT

The invention relates to compounds of the formula (I) and also liquid-crystal mixtures comprising these compounds, and their use in liquid-crystal displays:

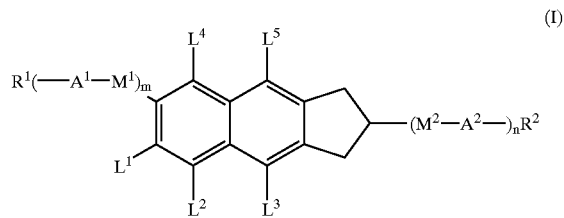

(I)

in which $R^1$ is H, F, $CF_3$, $OCF_3$, $OCF_2H$, $OCFH_2$, an alkyl radical or alkyloxy radical or an alkenyl radical or alkenyloxy radical, $R^2$ is H, an alkyl radical or alkyloxy radical or an alkenyl radical or alkenyloxy radical, $M^1$ and $M^2$ are $-C(=O)O-$, $-OC(=O)-$, $-CH_2O-$, $-OCH_2-$, $-OCF_2-$, $-CF_2O-$, $-C\equiv C-$, $-CH_2CH_2-$, $-CF_2CF_2-$, $-CF=CF-$ $C(=O)O-$ or a single bond $A^1$ and $A^2$ are $\alpha$-1,4-diyl, unsubstituted or mono- or disubstituted by F; where $\alpha$ is: phenylene cyclohexane, 1-cyclohexene, or 1,3-dioxane-2,5-diyl m and n are zero or 1; m+n=0 or 1

$L^1$, $L^2$, $L^3$, $L^4$ and $L^5$ are H or F.

16 Claims, 1 Drawing Sheet

OTHER PUBLICATIONS

Olsen, Robert J., et al., "A photoannulation route to naphthalenes from cyclic ketones", J. Org. Chem., 1991, 56; pp. 989–991.

Sakagami Sakumitsu, et al., "Mesomorphic properties of 2–(4–n–Alkoxybenzylideneamino)anthracenes", Bulletin of the Chemical Society of Japan, vol. 50(4), pp. 1009–1010 (1977).

Sigreist, A.E. von, et al., "Uber die darstellung von styryl–derivaten aus methyl–substituierten carbocyclischen aromaten", Helvatica Chimica Acta, vol. 52, fasc. 8 (1969), No. 253–254, pp. 2521–2554.

Haenel, Matthias W., et al., "Facile syntheses of 1,8–Bis-(diphenylphosphino)anthracene and 1,8–Bis(dimethylamino)anthracene by nucleophilic substitution of 1,8–difluoroanthracene", Synlett, Mar. 1998, pp. 301–303.

Cantrell, Gary L., "Synthesis of 1,2,3,4–tetrafluoro– and 1,2,3,4,5,6,7,8–octafluoroanthracenes via cycloaddition–revision", Journal of Fluorine Chemistry, 29 (1985), pp. 417–424.

Hankinson, B., et al., "Aryne chemistry, Part XXX, Approaches to the synthesis of 9–alkyl and 9,10–dialkyl–1, 2,3,4,5,6,7,8–octafluoro–9,10–dihydro–9,10–o–benzenoanthracenes (9–alkyl– and 9,10–dialkyl–1,2,3,4,5,6,7,8–octafluorotriptycenes)", J.C.S. Perkin I, 1972, pp. 2372–2377.

Kiefer, R., et al., "P2–30 In–Plane switching of nematic liquid crystrals", Japan Display, 1992, pp. 547–550.

Organikum, Organisch–Chemisches Grundpraktikum, Berlin 1984, pp. 612–616.

Cushman, Mark, et al., "Synthesis and evaluation of a series of benzylaniline hydrochlorides as potential cytotoxic and antimitotic agents acting by inhibition of tubulin polymerization", J. Med. Chem., 1993, 36, pp. 2817–2821.

Gray, G.W., et al., "The synthesis of several lateral difluoro–substituted 4,4"–dialkyl– and 4,4"–alkoxyalkyl–terphenyls and a rationalisation of the effect of such substitution on mesophase type and transition temperatures", Mol. Cryst. Liq. Cryst., 1991, vol. 204, pp. 43–64.

Bezborodov, V.S., et al., "The synthesis and properties of some mesomorphic cyclohexene derivatives" Liquid Crystals, 1997, vol. 23, No. 1, pp. 69–75.

Hird, Michael, et al., "The relationship between molecular structure and mesomorphic properties of 2,2'— and 3,2–difluoroterphenyls synthesized by palladium–catalysed cross–couplings", Liquid Crystals 1995, vol. 18, No. 1, pp. 1–11.

Schlosser, Manfred, "Superbase reactions: the expedient and selective metalation of fluorino– or trifluoromethyl–substituted benzenes", Synlett, Dec. 1990, pp. 747–748.

Butera, John, et al., "Computer–assisted design and synthesis of novel aldose reductase inhibitors", J. Med. Chem., 1989, 32, pp. 757–795.

Cha, Jin Soon, et al., "Preparations of aldehydes from carboxylic esters by reductive oxidations with lithium aluminum hydride and pryidinium chlorochromate or pyridinium dichromate", Bull. Korean Chem. Soc., 1999, vol. 20, No. 11, pp. 1373–1374.

Kanie, Kiyoshi, et al., "A convenient synthesis of trifluoromethyl ethers by oxidative desulfurization–fluorination of dithicarbonates", Bull. Chem. Soc. Jpn., 73, (2000), pp. 471–484.

Collins, J.C., "Dipyridine–chromium(VI) oxide oxidation of alcohols in dichloromethane", Tetrahedron Letter, No. 30, 1968, pp. 3363–3366.

Mongin, Florence, et al., "Regioselective ortho–lithiation of chloro and bromo substituted fluroarenes", Tetrahedron Letters, vol. 37, No. 36, pp. 6551–6554.

Colley, Robert A., "Linear and network polymer electrolytes based on low melting prepolymers", J. Mater. Chem., 1999, 9, pp. 1661–1667.

Gensler, Walter J., "Decarboxylative condensation. α–alkylcinnamic acids from aromatic aldehydes and alkylmalonic acids", J. American Chem. Soc., 80, Sep. 20, 1958, pp. 4949–4954.

Adcock, W., et al., "Substituent effects. VIII. Synthesis of substituted α– and β–fluoronaphthalenes", J. American Chem. Soc., 89:2, Jan. 18, 1967, pp. 386–390.

Mallory, Frank B., et al., "Substituent effects on through–space $^{19}F$–$^{19}F$ Coupling in the 1,8–difluoronaphthalene system", J. American Chem. Soc., 96:11, May 29, 1974, pp. 3536–3542.

Mitchell, Riginald H., et al., "Syntheses and reactions of the first dithia [3.1.3.1]metacyclophanes, [2.1.2.1]metacyclophanes, and [2.1.2.1]metacyclophanedienes", J. Org. Chem., 1984, 49, pp. 2534–2540.

Sucrow, Wolfgang, et al., "Einige nematische derivate des all–trans–perhydrophenanthrens", Chem. Ber., 118, 1985, pp. 3332–3349.

Coe, Paul Leslie, et al., "The lithiation of fluorinated benzenes and its dependence on solvent and temperature", J. Chem. Soc. Perkin Trans., 1995, pp. 2729–2737.

Li, Min–Hui, et al., "Blue phases and twist grain boundary phases (TGBA and TGBC) in a series of fluoro–substituted chiral tolane derivatives", Liquid Crystals, 1997, vol. 23, No. 3, pp. 389–408.

Larock, Richard, Comprehensive Organic Transformations, A Guide to Functional Group Preparations, 1989, VCH Publishers, Inc., New York, New York, title page and table of contents.

Ohmuro, K., et al., "33.3: Development of super–high–image–quality vertical–alignment–mode LCD", STD 97 Digest, pp. 845–848.

Jones, J.C., "Fast, high–contrast ferroelectric liquid crystal displays and the role of dielectric biaxiality", Diplays, vol. 14, No. 2, 1993, pp. 86–93.

Anderson, Benjamin A., et al., "Palladium–catalyzed cross coupling reactions of oxazol–2–ylzinc chloride derivatives", Synthesis, May 1996, pp. 583–585.

* cited by examiner

FLUORINATED CYCLOPENTA[B] NAPHTHALENES AND THEIR USE IN LIQUID-CRYSTAL MIXTURES

More and more applications of LCDs—for example, use in automobiles, where temperatures across a range from −40° C. to 100° C. may readily occur, and also for portable devices such as cell phones and notebook PCs—are requiring liquid-crystal mixtures combining a very wide range of operating temperatures with a very low threshold voltage.

Consequently there is an ongoing demand for new, appropriate liquid-crystal mixtures and components of such mixtures. As described in Ichinose et al. (IDW,00, Abstr. LCT4-3) or in DE-A-100 50 071, the search is on for materials possessing at the same time both high optical anisotropy (Δn) and low rotational viscosity, along with other parameters such as, for example, high absolute dielectric anisotropy (Δε) values, in addition to further application-relevant parameters.

It is an object of the present invention, therefore, to provide novel components for use in nematic or cholesteric or chiral smectic liquid-crystal mixtures which possess high absolute dielectric anisotropy values in combination with a favorable viscosity/clearing point relationship. Moreover, the compounds should be highly stable to light and UV and also to heat. Furthermore, they should be suitable for realizing high voltage holding ratios (VHRs). In addition, they should be readily available synthetically and thus potentially inexpensive.

DESCRIPTION OF THE DRAWINGS

For the purpose of illustrating the invention, the drawing provides additional information, which helps to define the invention.

Figure 1:
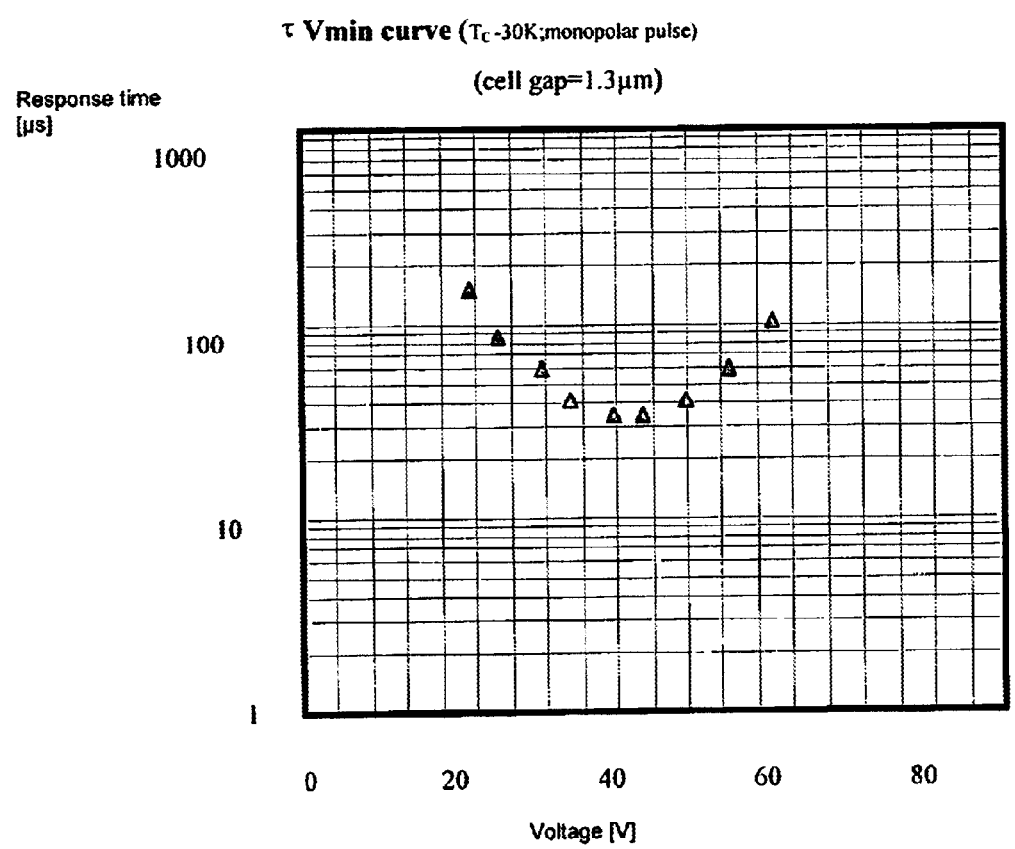
FIG. 1 is a voltage/response time curve, which illustrates the requirement for inverse mode operation.

It has now been found that these requirements are met by the fluorinated cyclopenta[b]naphthalenes of the formula (I)

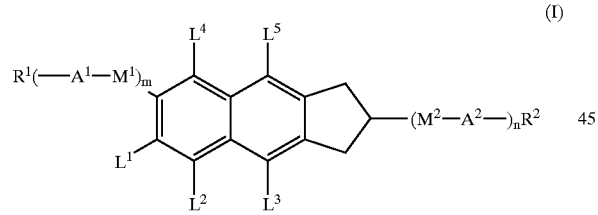

(I)

in which:
R$^1$ is H, F, CF$_3$, OCF$_3$, OCF$_2$H, OCFH$_2$, an alkyl radical or alkyloxy radical having from 1 to 12 carbon atoms or an alkenyl radical or alkenyloxy radical having from 2 to 12 carbon atoms, in which also in each case one (nonterminal) —CH$_2$— group (which is not adjacent to an oxygen) may have been replaced by —O— or C(=O)O—, one —CH$_2$— group may have been replaced by —C≡C— or cyclopropane-1,2-diyl and/or one or more H may have been replaced by F R$^2$ is H, an alkyl radical or alkyloxy radical having from 1 to 12 carbon atoms or an alkenyl radical or alkenyloxy radical having from 2 to 12 carbon atoms, in which also in each case one (nonterminal) —CH$_2$— group (which is not adjacent to an oxygen) may have been replaced by —O— or —C(=O)O—, one —CH$_2$— group may have been replaced by —C≡C— or cyclopropane-1,2-diyl and/or one or more H may have been replaced by F
with the proviso that R$^2$ may not be H if R$^1$ is H, F, CF$_3$, OCF$_3$, OCF$_2$H or OCFH$_2$ M$^1$ and M$^2$ independently of one another are —C(=O)O—, —OC(=O)—, —CH$_2$O—, —OCH$_2$—, —OCF$_2$—, —CF$_2$O—, —C≡C—, —CH$_2$CH$_2$—, —CF$_2$CF$_2$—, —CF=CF—C(=O)O— or a single bond A$^1$ and A$^2$ independently of one another are phenylene-1,4-diyl, unsubstituted or mono- or disubstituted by F; cyclohexane-1,4-diyl, unsubstituted or mono- or disubstituted by F; 1-cyclohexene-1,4-diyl, unsubstituted or monosubstituted by F; or 1,3-dioxane-2,5-diyl m and n independently of one another are zero or 1; m+n=0 or 1

L$^1$, L$^2$, L$^3$, L$^4$ and L$^5$ are H or F with the provisos that
a) at least one element from the group L$^1$, L$^2$, L$^3$, L$^4$, L$^5$ is F
b) L$^2$ and L$^3$ are only F if L$^4$ and L$^5$ are H
c) L$^5$ is only F if L$^4$ is F and L$^1$ is H.

Preference is given to the compounds of the formulae (Ia) to (In):

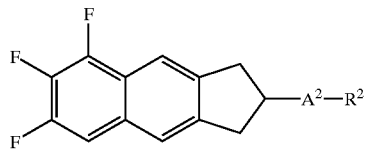

(Ia)

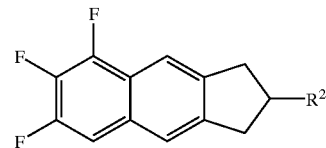

(Ib)

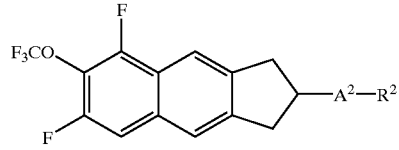

(Ic)

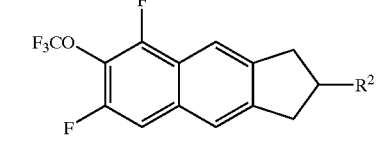

(Id)

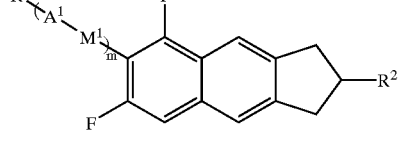

(Ie)

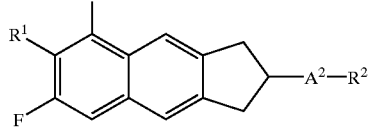

(If)

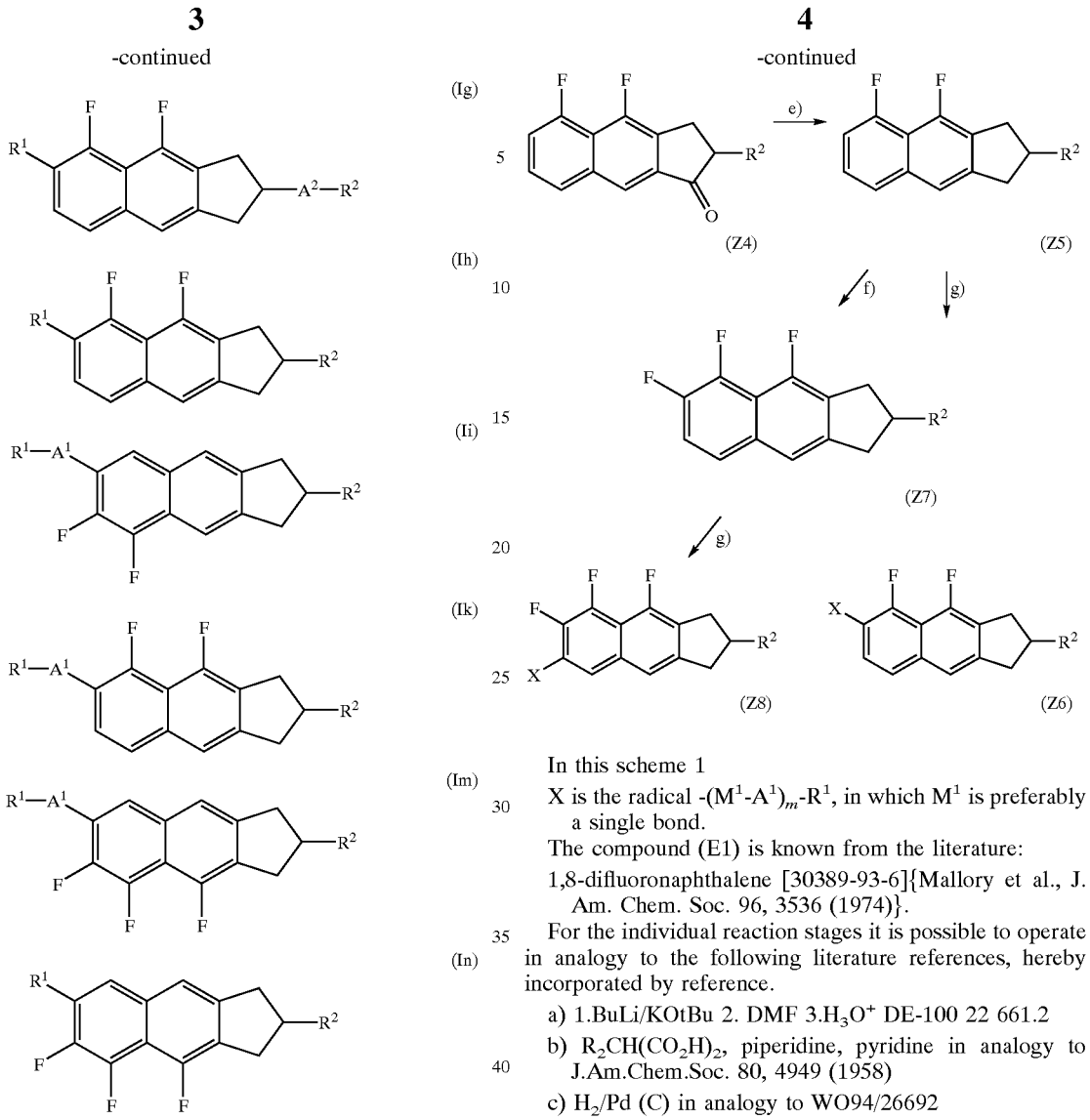

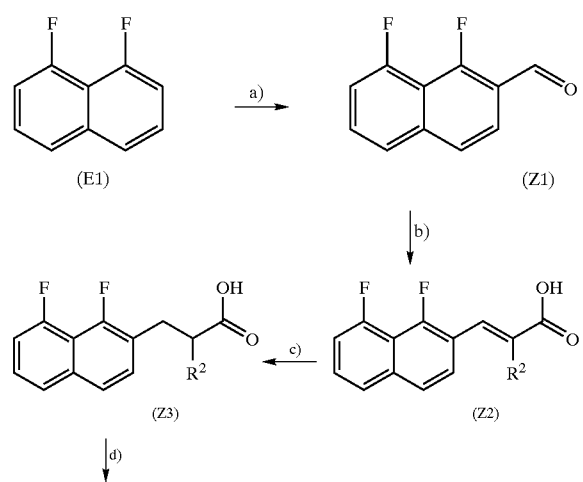

The synthesis of the compounds of the formulae (Ig)–(In) takes place in accordance with Scheme 1.

In this scheme 1

X is the radical $-(M^1-A^1)_m-R^1$, in which $M^1$ is preferably a single bond.

The compound (E1) is known from the literature:
1,8-difluoronaphthalene [30389-93-6]{Mallory et al., J. Am. Chem. Soc. 96, 3536 (1974)}.

For the individual reaction stages it is possible to operate in analogy to the following literature references, hereby incorporated by reference.

a) 1.BuLi/KOtBu 2. DMF 3.$H_3O^+$ DE-100 22 661.2 b) $R_2CH(CO_2H)_2$, piperidine, pyridine in analogy to J.Am.Chem.Soc. 80, 4949 (1958)

c) $H_2$/Pd (C) in analogy to WO94/26692 d) polyphosphoric acid in analogy to J.Med.Chem. 32(4), 757 (1989)

e) $Et_3SiH/F_3CCO_2H$ in analogy to DE-A-198 40 447.

f) 1. Metalation in analogy to J. Chem. Soc. Perkin Trans. I 1995 2729, Synlett 1990, 747 2. Reaction with an X-electrophile (in analogy to Tetrahedron 37, 6551 (1996)); on this point see also Schemes 4 to 7.

Here and in the schemes below, an X-electrophile is to be understood as referring to a functional derivative, as an electrophile, by way of which the group X can be introduced directly as such; it also refers, however, to a functional derivative which by way of a reaction sequence permits the synthesis of a substituent corresponding to X. Examples of X-electrophiles with which X can be introduced directly as such are alkyl halides (for X=$R^1$ when m=0) or NFSI (for X=F). One example of a reaction sequence for introducing X is the reaction with trimethylborate to give the corresponding boronic acid (X=$B(OH)_2$), the oxidation of that acid to the phenol (X=OH) and the conversion of said phenyl into the trifluoromethoxy compound (X=$OCF_3$) by the method of Hiyama (Bull.Chem.Soc.Jpn.73, 471 (2000)). The phenol may also, for example, be reacted with carboxylic acid or carboxylic acid derivatives to give compounds in which X is $R^1-A^1-C(=O)O-$. Another example of reaction sequences for introducing X is the reaction of the lithium compound with iodine (X=I) followed by Suzuki reaction with mesogenic boronic acids (R$^1$-A$^1$-B(OH)$_2$) to give compounds in which X is R$^1$-A$^1$-.

By "mesogenic" in this context are meant well-known building blocks of liquid-crystal compounds, typically featuring a para-(alkyl) substituent on a phenyl ring [which may have further substituents, including rings such as cyclohexane, for example, in an appropriate position (e.g., para)].

For the compounds (Ia) and (Ib) it is possible to use the synthesis according to scheme 2.

pentylphenyl)malonate [205760-95-8], diethyl 2-(4-hexylphenyl)malonate [29260-15-9], diethyl 2-(4-methylcyclohexyl)malonate [22273-84-3], diethyl 2-(4-ethylcyclohexyl)malonate [155378-91-9], diethyl 2-(4-propylcyclohexyl)malonate [100599-81-3], diethyl 2-(4-butylcyclohexyl)malonate [135564-27-1].

For the individual reaction stages it is possible to operate in analogy to the following literature references, hereby incorporated by reference.

a) 1. Mg 2. Oxirane 3. H$_3$O$^+$ 4. KMnO$_4$ 5. SOCl$_2$ in analogy to Larock, Comprehensive Organic

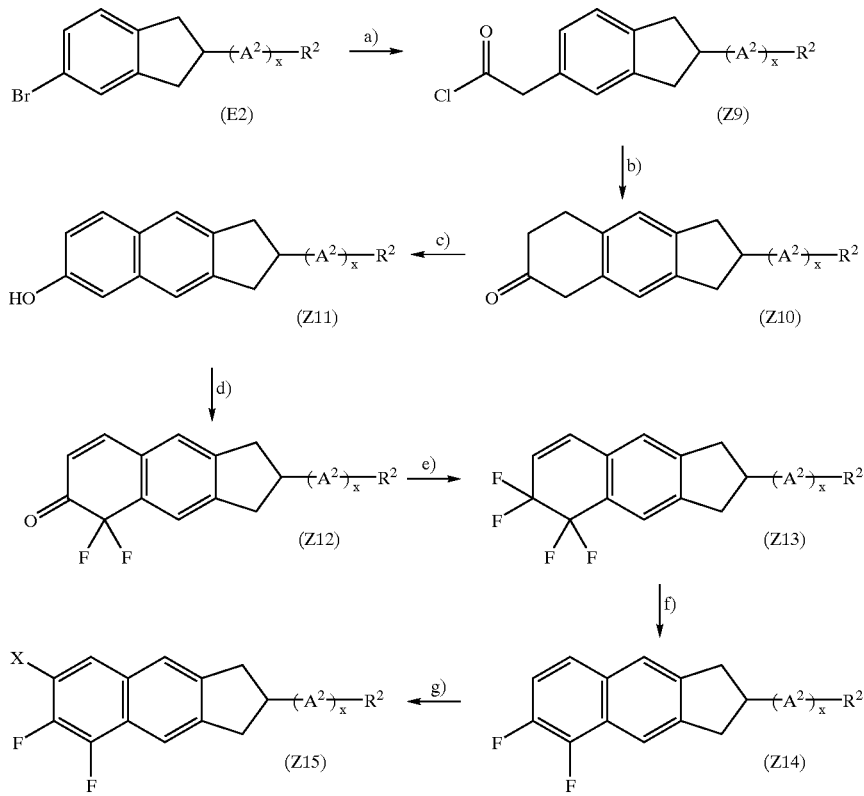

Scheme 2

In this scheme 2, x denotes 0 or 1

The starting materials (E2) are known from the literature:
x=0
5-Bromo-2-methyl-2,3-dihydro-1H-indene [88632-84-2], 5-bromo-2-octyl-2,3-dihydro-1H-indene [150636-27-4], and 5-bromo-2-decyl-2,3-dihydro-1H-indene [176317-00-3]; further homologs can be prepared analogously.
x=1

These compounds can be prepared in analogy to those where x=0 but replacing 2-alkylmalonic acids in the synthesis analogous to EP-A-546338 by 2-(4-alkylphenyl) malonic acids or 2-(4-alkylcyclohexyl)malonic acids. The following derivatives are known from the literature; further homologs can be prepared analogously: diethyl 2-(4-methylphenyl)malonate [29148-27-4], diethyl 2-(4-ethylphenyl)malonate [29148-28-5], diethyl 2-(4-propylphenyl)malonate [3585-46-4], diethyl 2-(4-butylphenyl)malonate [29148-30-9], dimethyl 2-(4-

Transformations, VCH Verlag, Weinheim 1989, ISBN 3-527-26953-3 b) H$_2$C=CH$_2$, AlCl$_3$, dichloromethane in analogy to EP-A-0 343 830

C) Pd (C), triglyme in analogy to Adcock, J. Am. Chem. Soc. 89, 386 (1967)

d) F-TEDA-BF$_4$, acetonitrile in analogy to EP-A-0 952 135 e) DAST, dichloromethane in analogy to EP-A-0 952 135 f) H$_2$, Pd/C, THF in analogy to EP-A-0 952 135 g) 1. metalation in analogy to J. Chem. Soc. Perkin Trans. I 1995 2729, Synlett 1990, 747 2. X-electrophile in analogy to Tetrahedron 37, 6551 (1996)); for this, see also schemes 4 to 7

The synthesis according to scheme 3 can be used for the compounds (Ic) to (If).

Scheme 3

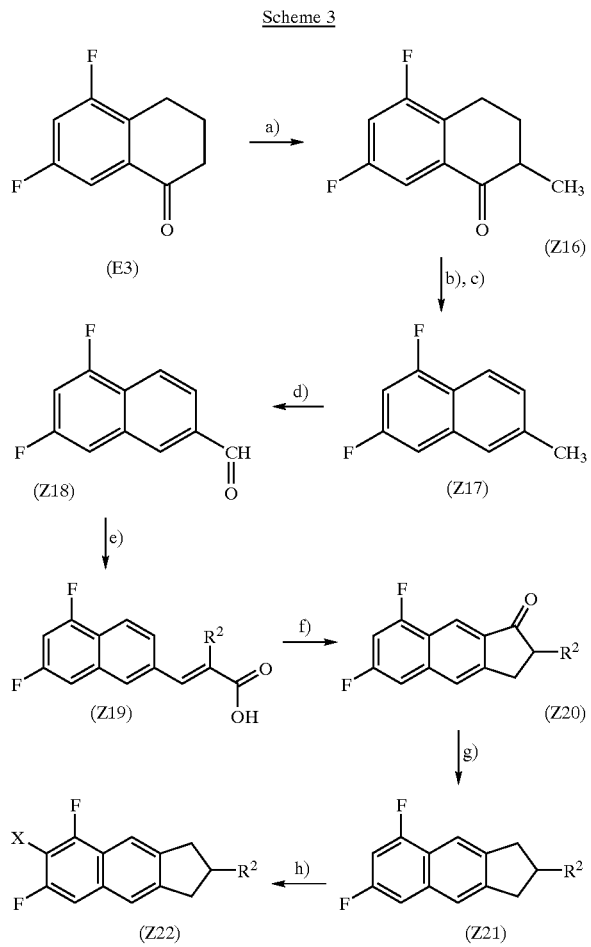

In this scheme 3

X is $R^1$-$(A^1$-$M^1)_m$-, where m can be 0 or 1

The starting material (E3) is known from the literature (J. Med. Chem. 1993, 36, 2819 U.S. Pat. No. 6,159,561). For the individual reaction stages it is possible to operate in analogy to the following literature references, hereby incorporated by reference.

a) 1. LDA 2. $CH_3I$ in analogy to U.S. Pat. No. 6,159,561 b) $Et_3SiH/F_3CCO_2H$ in analogy to U.S. Pat. No. 6,159,561 c) DDQ in analogy to U.S. Pat. No. 6,159,561 d) $SeO_2$, dioxane in analogy to Larock, Comprehensive Organic Transformations, VCH Verlag, Weinheim 1989, ISBN 3-527-26953-3 e) $R^2CH(CO_2H)_2$, piperidine, pyridine in analogy to J. Am. Chem. Soc. 80, 4949 (1958)

f) 1. $H_2$, Pd/C in analogy to WO 94/26692 2. polyphosphoric acid in analogy to J. Med. Chem. 32(4), 757 (1989)

g) $Et_3SiH/F_3CCO_2H$ in analogy to DE-A-198 40 447 h) metalation in analogy to J. Chem. Soc. Perkin Trans. I 1995 2729, Synlett 1990, 747 2. X-electrophile in analogy to Tetrahedron 37, 6551 (1996)); for this, see also schemes 4 to 7.

Generally speaking, cyclopenta[b]naphthalenes obtained in accordance with schemes 1, 2 and 3 and in which X=H (or Z5, Z7, Z14 and Z21 in schemes 1 to 3) may be reacted by metalation in this position and subsequent reaction with electrophiles (e.g., trimethylborate, DMF, $CO_2$, n-alkyl aldehydes, 4-n-alkylcyclohexanones, iodine, bromine) to give precursors from which the compounds of the formula (I) of the invention can be prepared (schemes 4 to 7).

Schema 4

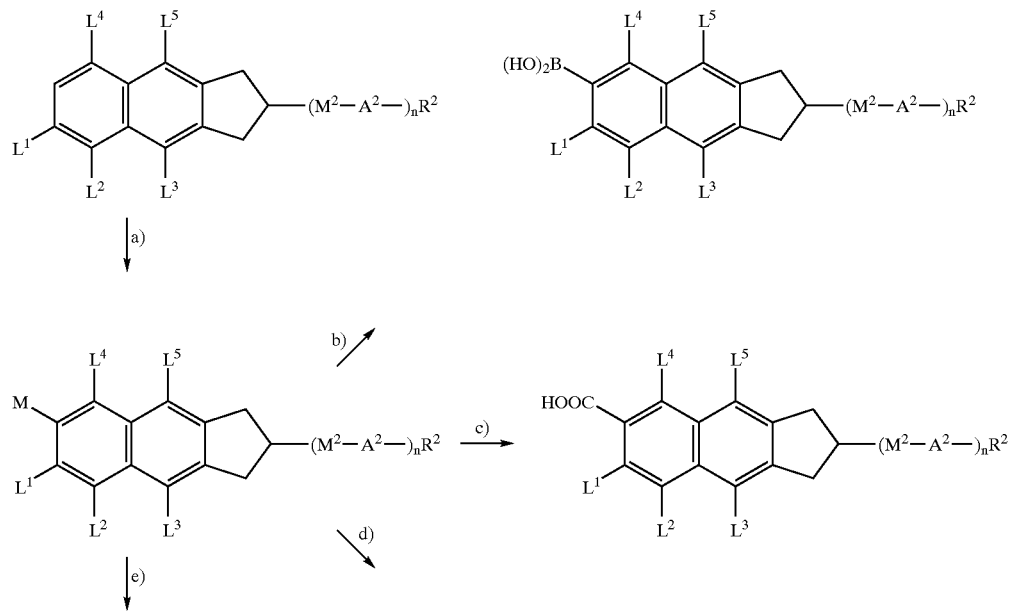

-continued
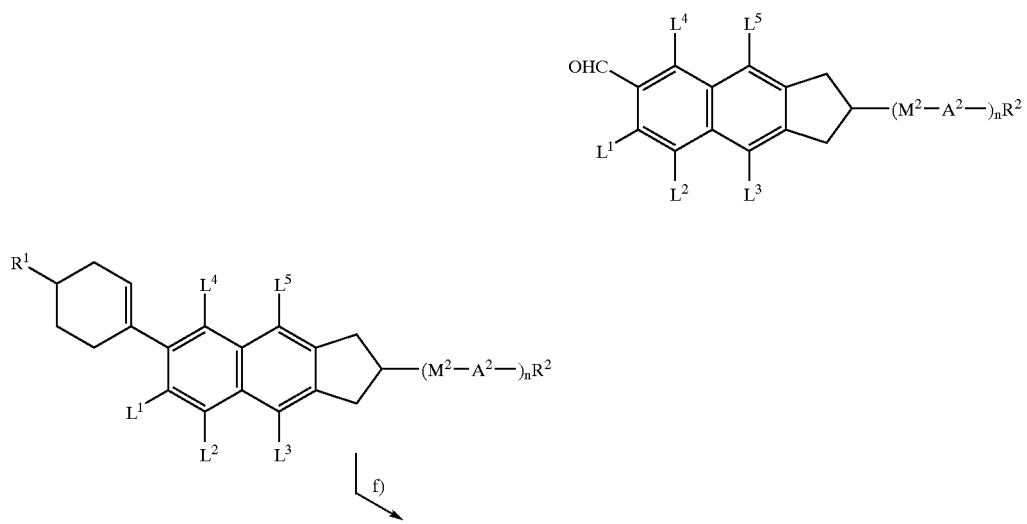
M = Li, K
a) n-BuLi/THF/hexane or n-BuLi/KOtBu/THF/hexane or sec-BuLi/THF/cyclohexane or LiTMP/THF/hexane
b) 1. B(OMe)$_3$ 2. H$_3$O$^+$
c) 1. CO$_2$ 2. H$_3$O$^+$ d) 1. DMF 2. H$_3$O$^+$
e) 1. 4-alkylcyclohexanone 2. H$_3$O$^+$ 3. cat. H$_2$SO$_4$/toluene
f) 4. H$_2$/Pd-C/toluene
Scheme 5
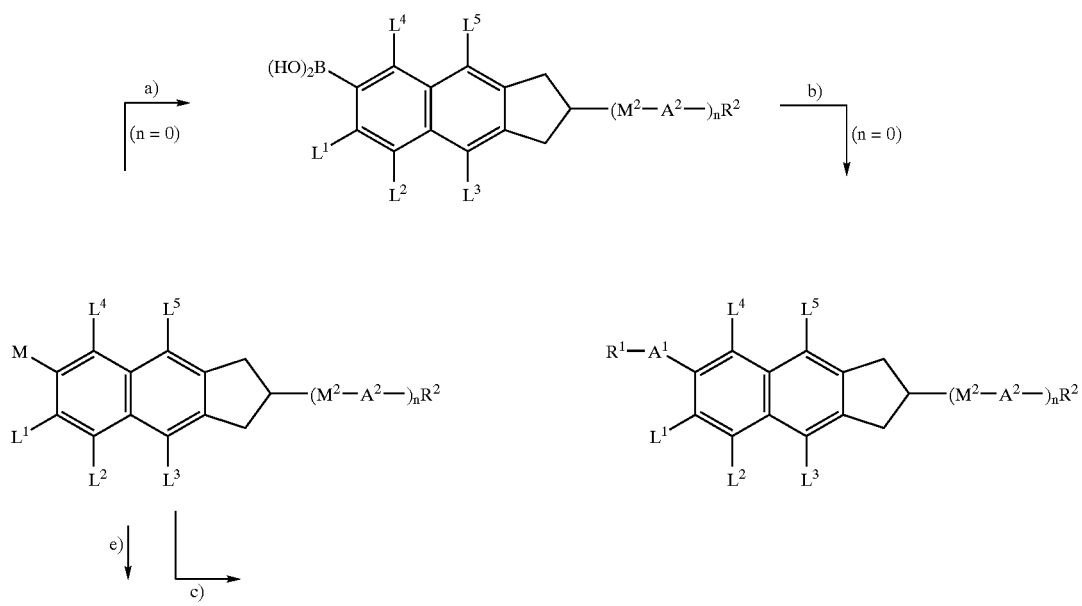

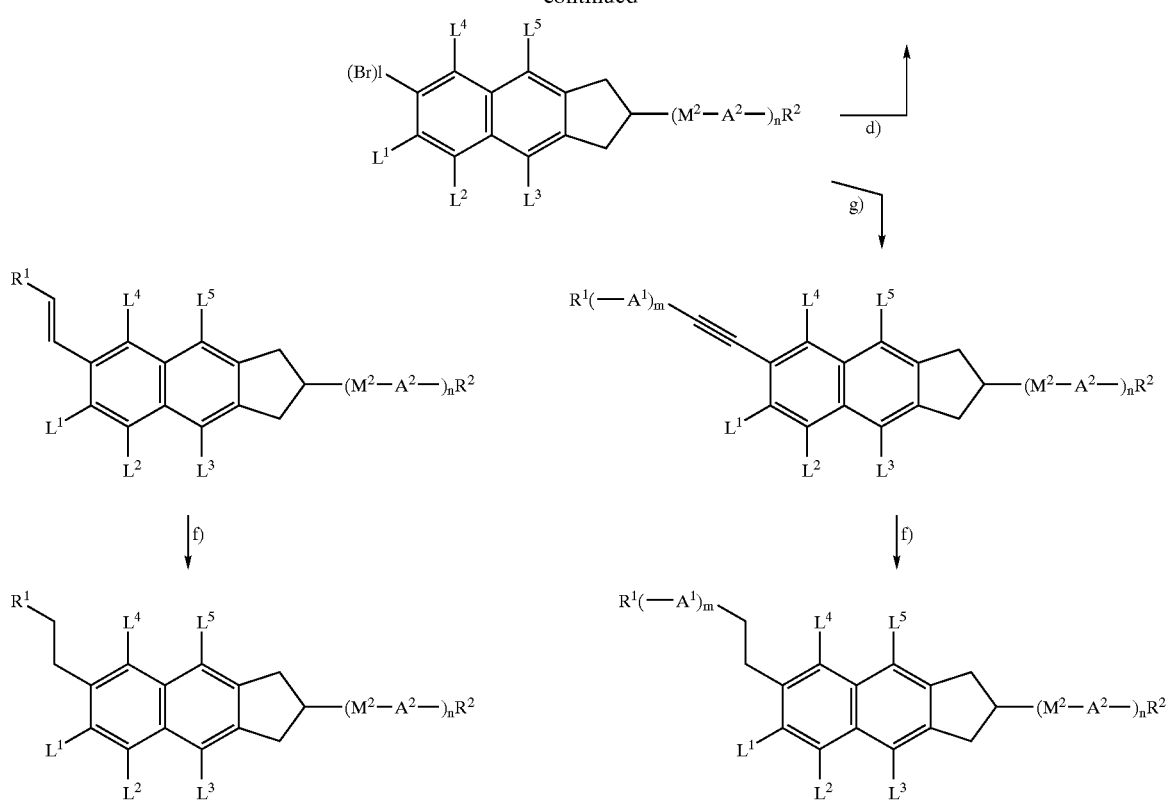
-continued
M = Li, K
a) 1. B(OMe)$_3$ 2. H$_3$O$^+$
b) R$^1$—A$^1$—Hal/Pd(PPh$_3$)$_4$/Na$_2$CO$_3$/toluene/EtOH/H$_2$O
c) I$_2$ (or Br$_2$)
d) R$^1$—A$^1$—B(OH)$_2$/Pd(PPh$_3$)$_4$/Na$_2$CO$_3$/toluene/EtOH/H$_2$O
e) 1. R$^1$—CH$_2$CHO 2. H$_3$O$^+$ 3. 4-TsOH/toluene
f) H$_2$/Pd-C/THF
g) R$^1$—(A$^1$)$_m$—C≡CH/Pd(PPh$_3$)$_2$Cl$_2$/CuI/NEt$_3$
Scheme 6
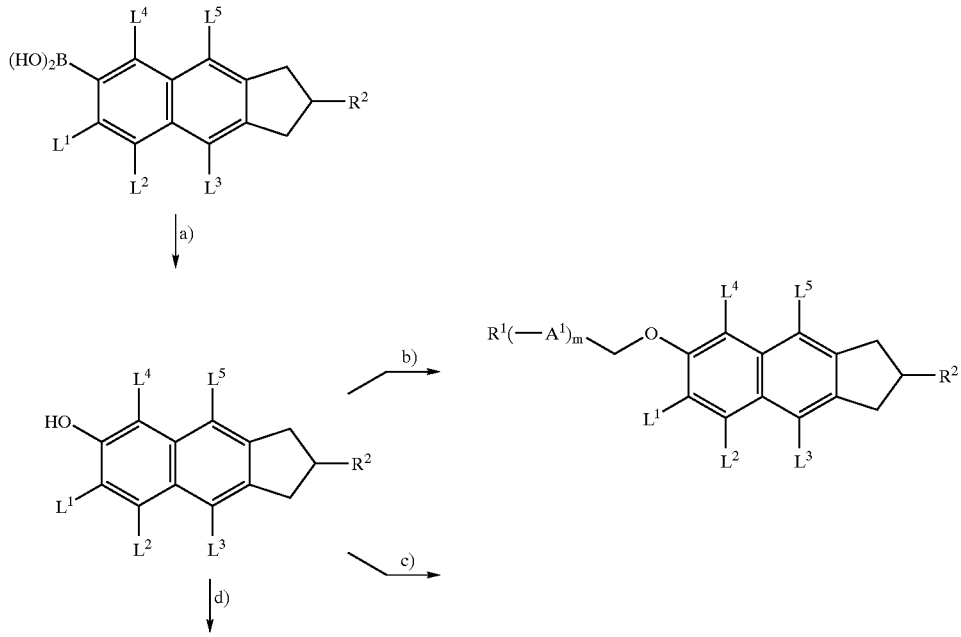

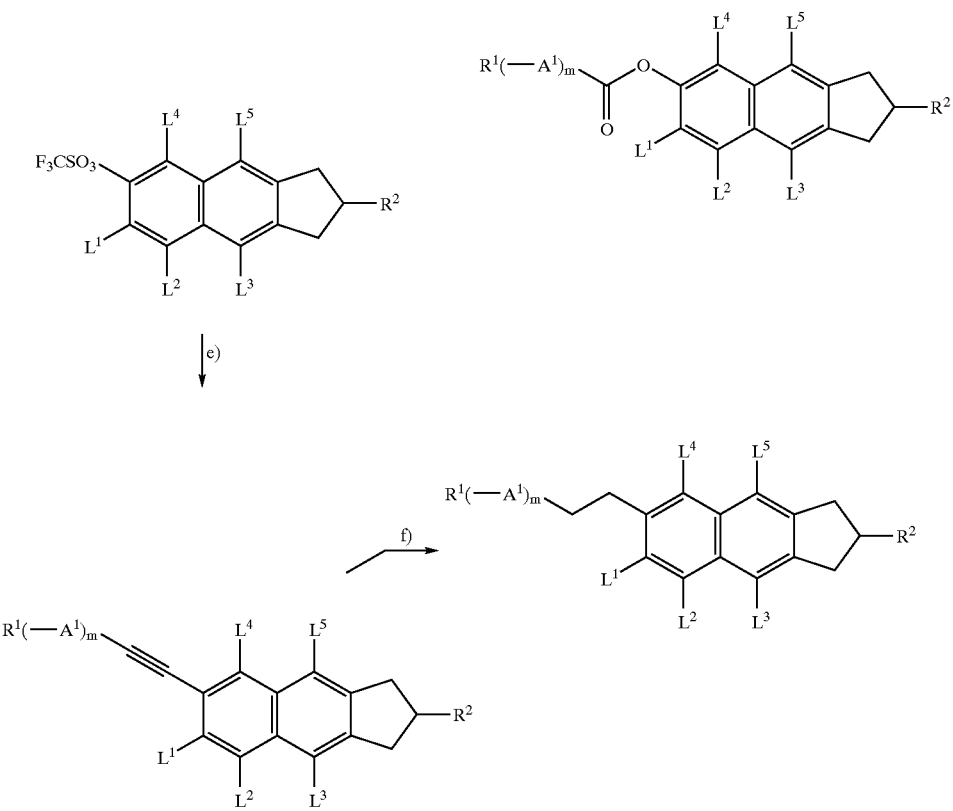
a) H$_2$O$_2$/MTBE
b) R$^1$(—A$^1$)$_m$—CH$_2$OH/DEAD/PPh$_3$/THF or R$^1$(—A$^1$)$_m$—CH$_2$Br/K$_2$CO$_3$/MEK
c) R$^1$(—A$^1$)$_m$—COOH/DCC/DMAP/CH$_2$Cl$_2$
d) (F$_3$CSO$_2$)$_2$O/pyridine
e) R$^1$(—A$^1$)$_m$—C≡CH/Pd(PPh$_3$)$_2$Cl$_2$/CuI/NEt$_3$
f) H$_2$/Pd—C/THF
Scheme 7
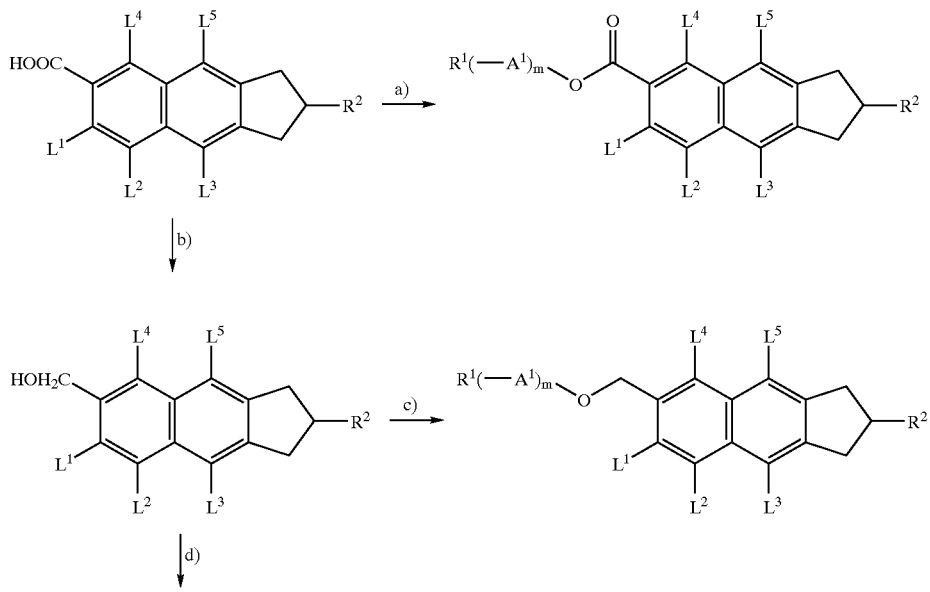

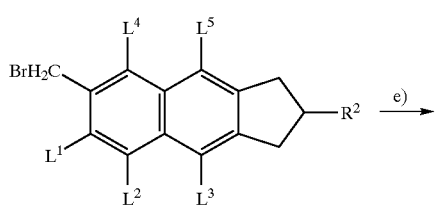
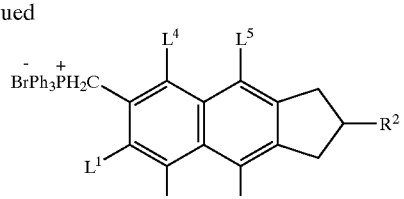

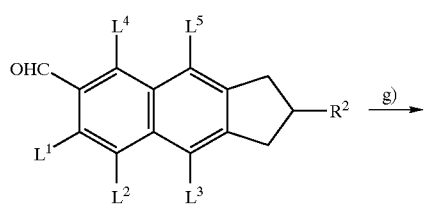
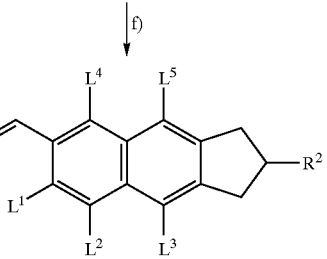

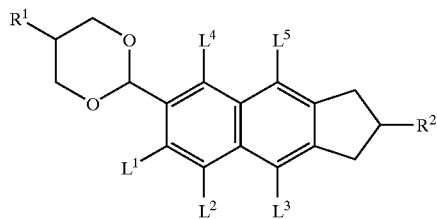
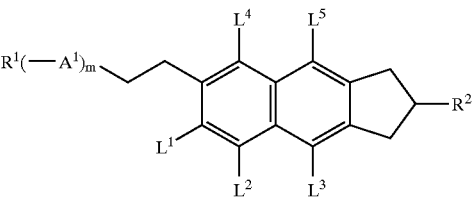

a) $R^1(-A^1)_m$-OH/DCC/DMAP/CH$_2$Cl$_2$
b) LiAlH$_4$/THF 2. H$_3$O$^+$
c) $R^1(-A^1)_m$-OH/DEAD/PPh$_3$/THF
d) PBr$_3$/CHCl$_3$
e) PPh$_3$/xylene
f) $R^1(-A^1)_m$-CHO/KOtBu/THF
g) $R^1(-A^1)_m$-CH$_2$P(Ph$_3$)Br/KOtBu/THF
h) $R^1$-CH(CH$_2$OH)$_2$/4-TsOH/toluene i) H$_2$/Pd-C/THF The preparation of the compounds required for the syntheses according to schemes 4 to 7, examples being alkyl-, alkenyl- or alkoxy-substituted, optionally additionally fluorinated benzoic acids, cyclohexanecarboxylic acids (scheme 6) phenylacetylenes (schemes 5 and 6), phenylboronic acids (scheme 5), bromobenzenes (scheme 5), 2-alkylpropane-1,3-diols (scheme 7), and 4-alkylcyclohexanones (scheme 4) and their reactions are known to the skilled worker and are described, for example, in WO 96/00710, WO 96/30344, Liq. Cryst. 1995, 18, 1, Mol. Cryst. Liq. Cryst. 1991, 204, 43, Liq. Cryst. 1997, 23, 389, Synthesis 1996, 589, WO 92/11241, EP-A 0665825, J. Mater. Chem. 1999, 9, 1669 and Chem. Ber. 1985, 118, 3332. Appropriately substituted benzyl alcohols and (hydroxymethyl)cyclohexanes are $R^2$-$A^2$-CH$_2$OH (scheme 6) can be obtained, for example, from the corresponding benzoic or cyclohexanecarboxylic acids $R^2$-$A^2$-COOH by reduction with lithium aluminum hydride (general procedure: Organikum, VEB Deutscher Verlag der Wissenschaften, 15th ed., Berlin 1984, section 7.3.4). Their bromination with phosphorus tribromide (in analogy to J. Org. Chem. 1984, 49, 2534–2540) provides the benzyl bromides and/or (bromomethyl)-cyclohexanes $R^2$-$A^2$-CH$_2$Br required in scheme 6. Subsequent reaction with triphenylphosphine in xylene gives the triphenylphosphonium bromides $R^2$-$A^2$-CH$_2$-P(Ph$_3$)Br which are mentioned in scheme 7. Correspondingly substituted benzaldehydes and cyclohexanecarboxaldehydes $R^2$-$A^2$-CHO (scheme 7) are available, for example, by reducing the respective carboxylic ester $R^2$-$A^2$-COOR (Bull. Korean Chem. Soc. 1999, 20, 1373) or oxidizing of the aforementioned benzyl alcohols and (hydroxymethyl)cyclohexanes $R^2$-$A^2$-CH$_2$OH (Tetrahedron Lett. 1968, 30, 3363).

Starting from the 6-hydroxy-substituted cyclopenta[b] naphthalenes (scheme 6) it is also possible, for example, to prepare the corresponding 6-trifluoromethoxy-substituted compounds of the formulae (Ic) and (Id) (Bull. Chem. Soc. Jpn. 2000, 73, 471).

The synthesis of specific radicals X takes place, for example, in accordance with DE-A 19528085, DE-A 19532292 and DE-A 19654487. Inventive compounds of the formula (I) with a 1-cyclohexene-1,4-diyl or 2-fluoro-1-cyclohexene-1,4-diyl- or 4-fluoro-3-cyclohexen-1-yl unit are prepared as described in Liq. Cryst. 1997, 23, 69, DE-A 4427266, DE-A 19607996, DE-A 19528665 and EP-A 0736513. As far as the synthesis of specific radicals $R^1$ and $R^2$ is concerned, reference may also be made, for example, to U.S. Pat. No. 4,798,680 (for optically active compounds with a 2-fluoroalkyloxy unit) and EP-A 0 318 423 (for compounds containing cyclopropyl groups in the side chain).

The compounds of the formula (I) are used preferably in nematic or cholesteric liquid-crystal mixtures. The liquid-crystal mixtures of the invention comprise at least one compound of the formula (I), preferably in an amount from 1 to 40% by weight, based on the liquid-crystal mixture. They preferably comprise at least 3 further components. The selection of these further compounds (e.g., from the types listed in DE-A-19629812, pages 12 to 16) and the preparation of the liquid-crystal mixtures are familiar to the skilled worker.

The invention further provides a liquid-crystal display comprising these liquid-crystal mixtures. This liquid-crystal display preferably operates in IPS display mode (Kiefer et al., Japan Display '92, p. 547) or in VA display mode (Ohmura et al., SID 97 Digest, p. 845) or in ECB display mode (EP-A-0 474 062).

Preference is likewise given to using the compounds of the formula (I) in chiral smectic liquid-crystal mixtures. The liquid-crystal mixtures of the invention comprise at least one compound of the formula (I), preferably in an amount of from 1 to 40% by weight, based on the liquid-crystal mixture. They preferably comprise at least 3 further components. These components are preferably selected from the known compounds having smectic and/or nematic and/or cholesteric phases. The selection of these further compounds (e.g., from the types listed in DE-A-19857352) and also the preparation of the liquid-crystal mixtures are familiar to the skilled worker.

The invention also provides a liquid-crystal display comprising these liquid-crystal mixtures.

The invention is illustrated by the examples below.

EXAMPLE 1

A chiral smectic liquid-crystal mixture M1 having the melting point 7° C. is admixed with 10% by weight of the compound 4,5-difluoro-6-hexyl-2-pentyl-2,3-dihydro-1H-cyclopenta[b]naphthaline [(Ih) where $R^1$=hexyl, $R^2$=pentyl; obtained from the reaction sequence according to scheme 1]. The resulting mixture has a melting point of 0° C. The voltage/response time curve (FIG. 1) has the minimum required for inverse mode operation (e.g., "Fast High Contrast Ferroelectric Liquid Crystal Displays and the Role of Dielectric Biaxiality" by J. C. Jones, M. J. Towler, J. R. Hughes, Displays, Volume 14, No. 2(1993) 86–93 or M. Koden, Ferroelectrics 179, 121(1996)); the values achieved are within the industrially relevant range and the mixture is suitable for practical use.

EXAMPLE 2

A nematic liquid-crystal mixture M2 consisting of 50% by weight of 1-(3,4-difluorophenyl)-4-(4-vinyl)cyclohexyl-cyclohexane and 50% by weight of 1-[4-(3-butenyl)cyclohexyl]-4-(3,4-difluorophenyl)cyclohexane is admixed with 20% by weight of the compound 2-propyl-5,6,7-trifluoro-2,3-dihydro-1H-cyclopenta[b]naphthalene [(Ib) where $R^2$=propyl; obtained from the reaction sequence according to Scheme 3]; as a result of the addition of the compound of the invention, the dielectric anisotropy Δε has risen from 4.8 to 5.6.

What is claimed is:

1. A compound of the formula (I)

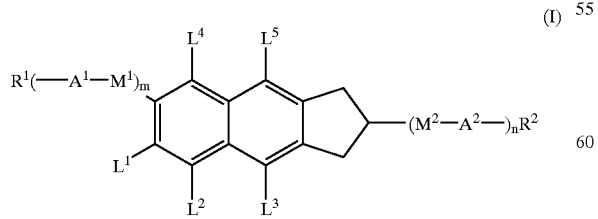

(I)

in which
$R^1$ is H, F, $CF_3$, $OCF_3$, $OCF_2H$, $OCFH_2$, an alkyl radical or alkyloxy radical having from 1 to 12 carbon atoms or an alkenyl radical or alkenyloxy radical having from 2 to 12 carbon atoms, in which also in each case one (nonterminal) —$CH_2$— group (which is not adjacent to an oxygen), may have been replaced by —O— or —C(=O)O—, one —$CH_2$— group may have been replaced by —C≡C— or cyclopropane-1,2-diyl and/or one or more H may have been replaced by F $R^2$ is H, an alkyl radical or alkyloxy radical having from 1 to 12 carbon atoms or an alkenyl radical or alkenyloxy radical having from 2 to 12 carbon atoms, in which also in each case one (nonterminal) —$CH_2$— group may have been replaced by —O— or —C(=O)O—, one —$CH_2$— group (which is not adjacent to an oxygen) may have been replaced by —C≡C— or cyclopropane-1,2-diyl and/or one or more H may have been replaced by F with the proviso that $R^2$ may not be H if $R^1$ is H, F, $CF_3$, $OCF_3$, $OCF_2H$ or $OCFH_2$ $M^1$ and $M^2$ independently of one another are —C(=O)O—, —OC(=O)—, —$CH_2$O—, —O$CH_2$—, —$OCF_2$—, —$CF_2$O—, —C≡C—, —$CH_2CH_2$—, —$CF_2CF_2$—, —CF=CF—C(=O)O— or a single bond $A^1$ and $A^2$ independently of one another are phenylene-1,4-diyl, unsubstituted or mono- or disubstituted by F; cyclohexane-1,4-diyl, unsubstituted or mono- or disubstituted by F; 1-cyclohexene-1,4-diyl, unsubstituted or monosubstituted by F; or 1,3-dioxane-2,5-diyl m and n independently of one another are zero or 1; m+n=0 or 1

$L^1$, $L^2$, $L^3$, $L^4$ and $L^5$ are H or F with the provisos that
a) at least one element from the group $L^1$, $L^2$, $L^3$, $L^4$, $L^5$ is F
b) $L^2$ and $L^3$ are only F if $L^4$ and $L^5$ are H
c) $L^5$ is only F if $L^4$ is F and $L^1$ is H.

2. A compound as claimed in claim 1, corresponding to one of the formulae (Ia) to (In)

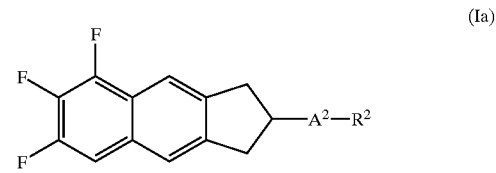

(Ia)

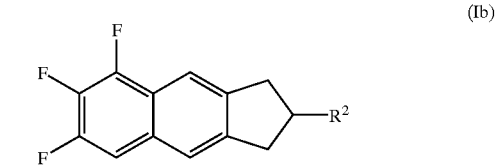

(Ib)

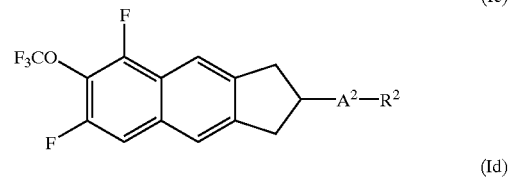

(Ic)

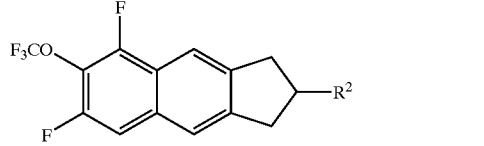

(Id)

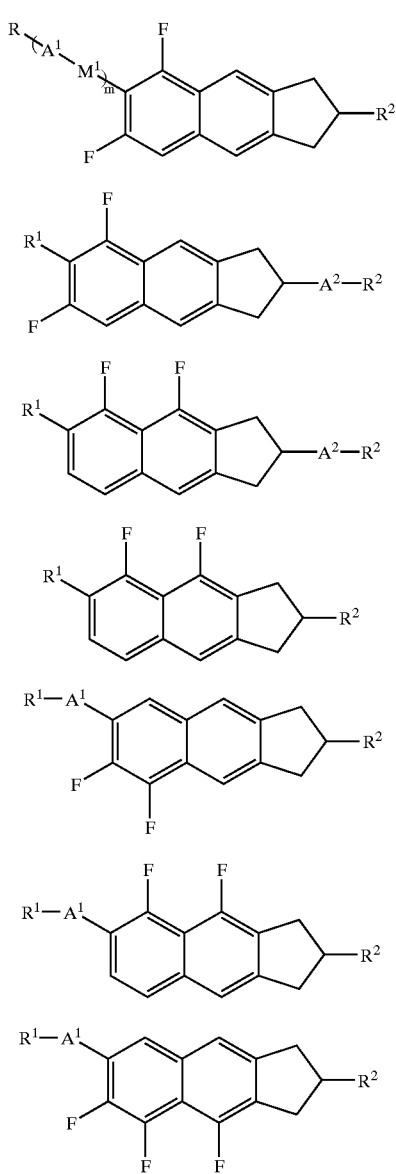

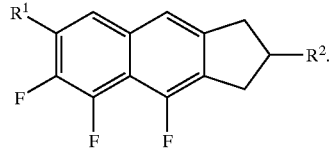

3. A liquid-crystal mixture, comprising one or more compounds as claimed in claim 1 in liquid-crystal mixtures.

4. A liquid-crystal mixture, comprising one or more compounds as claimed in claim 2.

5. The liquid-crystal mixture as claimed in claim 3, which comprises one or more compounds of the formula (I) in an amount of from 1 to 40% by weight, based on the liquid-crystal mixture.

6. The liquid-crystal mixture as claimed in claim 3, which comprises at least three further components of smectic and/or nematic and/or cholesteric phases.

7. The liquid-crystal mixture as claimed in claim 3, which is chiral smectic.

8. The liquid-crystal mixture as claimed in claim3, which is nematic or cholesteric.

9. A liquid-crystal display comprising a liquid-crystal mixture as claimed in claim 3.

10. The liquid-crystal display, which is operated in ECB, IPS or VA display mode and comprises a liquid-crystal mixture as claimed in claim 8.

11. The liquid-crystal mixture as claimed in claim 4, which comprises one or more compounds of the formula (I) in an amount of from 1 to 40% by weight, based on the liquid-crystal mixture.

12. The liquid-crystal mixture as claimed in claim 4, which comprises at least three further components of smectic and/or nematic and/or cholesteric phases.

13. The liquid-crystal mixture as claimed in claim 4, which is chiral smectic.

14. The liquid-crystal mixture as claimed in claim 4, which is nematic or cholesteric.

15. A liquid-crystal display comprising a liquid-crystal mixture as claimed in claims 4.

16. The liquid-crystal display, which is operated in ECB, IPS or VA display mode and comprises a liquid-crystal mixture as claimed in claim 14.

* * * * *